United States Patent [19]

Mizukuchi

[11] 4,216,109

[45] * Aug. 5, 1980

[54] LIQUID CRYSTAL COMPOSITION AND METHOD FOR MAKING SAME

[75] Inventor: Yutaka Mizukuchi, Saitama, Japan

[73] Assignee: Citizen Watch Co., Ltd., Tokyo, Japan

[*] Notice: The portion of the term of this patent subsequent to Feb. 6, 1995, has been disclaimed.

[21] Appl. No.: 960,595

[22] Filed: Nov. 14, 1978

Related U.S. Application Data

[63] Continuation-in-part of Ser. No. 771,991, Feb. 25, 1977, Pat. No. 4,138,359.

[30] Foreign Application Priority Data

May 25, 1976 [JP] Japan .................... 51/59629

[51] Int. Cl.² ............................ C09K 3/34; G02F 1/13
[52] U.S. Cl. ................................. 252/299; 252/408; 260/465 D; 350/350 R; 560/20; 560/73; 560/107
[58] Field of Search ................. 252/299, 408; 350/350; 260/465 D; 560/20, 73, 107

[56] References Cited

U.S. PATENT DOCUMENTS

| | | | |
|---|---|---|---|
| 3,772,389 | 11/1973 | Lowrance, Jr. | 260/465 D |
| 3,925,238 | 12/1975 | Gavrilovic | 252/299 |
| 3,947,375 | 3/1976 | Gray et al. | 252/299 |
| 3,951,846 | 4/1976 | Gavrilovic | 252/299 |
| 3,952,046 | 4/1976 | Scherrer et al. | 260/463 |
| 3,953,491 | 4/1976 | Steinstrasser et al. | 252/299 |
| 3,971,824 | 7/1976 | Van Meter et al. | 252/299 |
| 4,009,934 | 3/1977 | Goodwin et al. | 252/299 |
| 4,017,416 | 4/1977 | Inukai et al. | 252/299 |
| 4,029,594 | 6/1977 | Gavrilovic et al. | 252/299 |
| 4,035,056 | 7/1977 | Coates et al. | 252/299 |
| 4,065,489 | 12/1977 | Steinstrasser et al. | 252/299 |
| 4,073,742 | 2/1978 | Erdman et al. | 252/299 |
| 4,099,856 | 7/1978 | Weissflog et al. | 252/299 |
| 4,112,239 | 9/1978 | Dubois et al. | 252/299 |
| 4,138,359 | 2/1979 | Mizukuchi | 252/299 |

FOREIGN PATENT DOCUMENTS

| | | | |
|---|---|---|---|
| 2348193 | 4/1974 | Fed. Rep. of Germany | 252/299 |
| 2600558 | 7/1976 | Fed. Rep. of Germany | 252/299 |
| 48-75484 | 11/1973 | Japan | 252/299 |
| 49-95880 | 9/1974 | Japan | 252/299 |

OTHER PUBLICATIONS

Gray, G. W., et al., "Liquid Crystals & Plastic Crystals", vol. 1, John Wiley & Sons, Inc., N.Y., pp. 100–152 (1974).

*Primary Examiner*—Teddy S. Gron
*Attorney, Agent, or Firm*—Koda and Androlia

[57] ABSTRACT

A new and novel liquid crystal composition having broad temperature and chemical stability is disclosed. The liquid crystal composition comprises a compound having the general formula:

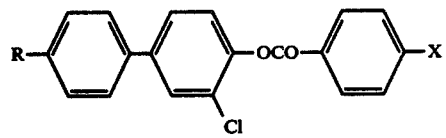

(R represents an alkyl or alkoxyl group and X represents an alkyl, alkoxyl, nitro or cyano group).

The method for making the liquid crystal compound includes the methylation of 4-phenyl-2-chlorophenol and like compounds.

7 Claims, No Drawings

LIQUID CRYSTAL COMPOSITION AND METHOD FOR MAKING SAME

This is a continuation-in-part application of Ser. No. 771,991 filed Feb. 25, 1977, now U.S. Pat. No. 4,138,359.

BACKGROUND OF THE INVENTION

1. Field of the Invention

This invention relates to liquid crystal compositions which include a specific biphenyl-like liquid crystal material and the method for making the same.

2. Prior Art

The use of liquid crystal materials in timepieces and the like are well-known in the art. Displays including these liquid crystal materials are often referred to as liquid-crystal displays (LCDs) which are not self illuminating; they simply absorb or scatter ambient light and thus operate either as a reflective or a transmissive mode. The LCD is turned on and made visible by a voltage-controlled change in the refractive index of the display medium. Nematic liquid-crystals presently dominate the liquid-crystal display technology. The word "nematic" is derived from the Greek word for thread and refers to microscopic thread-like boundaries separating the LC medium's various domains of molecular orientation. The term "liquid crystal" refers to the nature of the display medium; it is organic, and pours, flows and otherwise behaves as a normal liquid, yet its cigar-shaped molecules have an orderliness that makes the fluid behave optically like a crystal.

Apart from the nematic, the cholesteric type of liquid crystals is one the few other LC phases of current interest in display technology. Cholesteric liquid crystals change color under the influence of temperature and pressure, for example, but mixtures of these liquid crystals have had problems in terms of their storage stability properties. In a typical display device, the basic display consists of a thin layer of LC solution sandwiched between two thin glass plates. A transparent electrode material, usually tin oxide, forms a 7-segment numeral on the inside surface of the front plate, as well as a non-segmented electrode pattern on the inside surface of the rear plate. In reflective structures, a highly-reflective electrode material, such as chromium, aluminum or nickel, which serves as a mirror, is deposited on the rear plate.

In its quiescent state, the LC medium is transparent, (i.e., the display is dark) because of the orderly array of its cigar-shape molecules. When a voltage is applied between the electrodes, an electric field is created that disorders the LC molecules, thus rendering the medium opaque in the vicinity of the field, scattering the light. The segmented electrodes selectively activate the medium; activated areas appear brighter than the unactivated areas, and a numeral appears. This type of operation is generally referred to in the art as dynamic scattering. Because light is scattered away (in the same direction as that of the incident light), dynamic scattering operation requires a reflector when the observer's eye is in front of the LC cell, as in a watch display. Direct-current operation shortens life, therefore, such display use an AC drive signal.

Field-effect LCD's transmit polarized light in their quiescent state and block it in the presence of an electric field. Current flow is not necessary, as in the dynamic-scattering mode. In a field-effect LCD, the preferred alignment of molecules near one glass plate is at 90 degrees to the alignment near the other plate. In effect, the LC molecule alignment is twisted through 90 degrees across the thickness of the cell. Thus, field-effect operation is also referred to as twisted-nematic operation.

Although the basic cell structure is the same as that of the dynamic-scattering cell, polarizer elements are added, crossed at 90 degrees, at the front and rear plates. Polarized light enters the unactivated cell, is rotated 90 degrees by the molecular twist of the LC medium, and thus exits the cell through the cross-polarizer of the rear. When activated by an electric field, the molecular alignment "straightens-out", and passes the polarized incident light directly to the rear cross-polarizer without further rotation. The rear polarizer now blocks the light, and an observer behind the cell sees a dark display on a light background. Angularly aligning the polarizers creates a light display on a dark background. Placing a mirror behind the second polarizer creates a reflective cell.

Reflective field effect LCD's provide a significantly higher contrast ratio and thus are generally easier to read than reflective dynamic-scattering devices. It is also possible to generate color in field effect displays; however, the same problem is present, namely, the use of the liquid crystal material therein to create such color and light scattering is not thermally or chemically stable.

Thus, the above-identified problems are of significant proportions given the fact that chemical contamination, including impurities from the glass, and discoloration, can render the entire display device useless. Shortened lifetime and poor performance results from contaminated LC material and is further enhanced because the rate of decomposition is accelerated when the device is turned on.

Examples of electrochromatic displays are disclosed in U.S. Pat. No. 3,839,857 and U.S. Pat. No. 3,652,149.

When one traces the history of the materials used in such display elements, a variety of liquid crystal materials have been developed and introduced. Among those materials used include biphenyl liquid crystals and ester liquid crystal. These type of liquid crystals have been used because of their relatively good colorlessness and chemical stability. However, these prior art materials, by themselves, have a rather narrow temperature stability range and therefore are generally used as a mixed composition with other more temperature stable materials. For example, the operating temperature range of typical biphenyl liquid crystal material is as follows:

| | Liquid Crystal Operating Temperature Range |
|---|---|
| $C_5H_{11}$—⟨ ⟩—⟨ ⟩—CN (1) | 22°–35° C. |
| $C_6H_{13}$—⟨ ⟩—⟨ ⟩—CN (2) | 58°–76° C. |
| Equal mixture by mole of (1) and (2) | 10°–55° C. |

In the case of ester based liquid crystals

| | |
|---|---|
| $C_7H_{15}$—⟨ ⟩—COO—⟨ ⟩—CN | −42° C. |

-continued

| General Formula | |
|---|---|
| C₅H₁₁O—⟨⟩—OCO—⟨⟩—OCO₂C₅H₁₁ | 45°–72° C. |
| C₇H₁₅O—⟨⟩(Cl)—COO—⟨⟩—OC₄H₉ | 45°–70° C. |

As described above, these conventional biphenyl and ester liquid crystal materials have a generally narrow temperature range for displaying purposes. The lowest point of the temperature range indicates the transient temperature from solid state to nematic state and the highest point indicates the transient temperature from nematic state to isotropic state.

The purpose of this invention is to provide a liquid crystal material which has excellent chemical stability, at least as good as the biphenyl liquid crystal materials and estel liquid crystal materials and, in addition, has a broad range of temperature stability. In order to achieve this object, biphenyl benzoyl ester having a lateral chlorine substitution is derived.

The novel features which are believed to be characteristic of the invention, both as its organization and method of operation, together with further objectives and advantages thereof, will be better understood from the following description in which presently preferred embodiments of the invention are illustrated by way of examples. It is to be expressly understood, however, that the examples are for the purpose of illustration and description only and are not intended as a definition of the limits of the invention.

DESCRIPTION OF THE PREFERRED EMBODIMENTS

The typical liquid crystal materials of the present invention and their operating temperature range are as follows:

| | General Formula | Liquid Crystal Temperature Range |
|---|---|---|
| Compound 1 | C₈H₁₇—⟨⟩—⟨⟩(Cl)—OCO—⟨⟩—OC₈H₁₇ | 55°–115° C. |
| Compound 2 | C₈H₁₇—⟨⟩—⟨⟩(Cl)—OCO—⟨⟩—C₈H₁₇ | 36°–86° C. |
| Compound 3 | C₈H₁₇—⟨⟩—⟨⟩(Cl)—OCO—⟨⟩—NO₂ | 74°–104° C. |

The methods for making the compounds of the present inventions and examples of liquid crystal compositions comprising these compounds are described hereinbelow.

EXAMPLE 1

4-phenyl-2-chlorophenol is methylated by means of well-known method steps and 4-phenyl-2-chloroanisole (hereinafter referred to as Material I) is extracted. ⅓ mole of Material I is dissolved into carbon disulfide 300 cc and a Friedel-Craft's reaction is effected a MILO flask in which ⅓ mole of octanol chloride and 60 grams of anhydrous ammonium chloride are placed. As a result, 4-octanoyl-4'-methoxy-3'-chlorobiphenyl (hereinafter referred to as Compound 4) is extracted with a yield of 75%. As the result of reduction of said Compound 4, by the well-known Wolff-Kischner's reaction, 4-octyl-4'-methoxy-3'-chlorobiphenyl (hereinafter referred to as Compound 5) is extracted with a yield of 70 weight percent. 0.01 mole of 4-octyl-4'-hydroxy-3-chlorobiphenyl (hereinafter referred to as Material II) which is extracted from said Compound 5 by means of demethylation with HBr water, is dissolved into mixed solution of 100 cc of pyridine and 50 cc of benzene. After this 0.012 mole of 4-octyloxy benzoic chloride is added to the solution, this mixed solution is heated and stirred for 24 hours. An extraction process is achieved by adding water (200 cc) and benzene (100 cc) into the solution. The resultant benzene layer is washed with a mixture of 1 mole of sodium hydroxide solution (50 cc) and 1 mole of HCl liquid (100 cc). After the resultant compound in benzene layer is left through the washing, it is crystallized from ethyl alcohol (50 cc). The result of the above method steps, 4-octyl-4'-(4"-octyloxy benzoil)-3'-chrobiphenyl (Compound 1 in the above table) is extracted at the yield rate of 85%.

EXAMPLE 2

0.01 mole of said Material II is dissolved into 30 cc of alcohol to which are added 0.6 grams of KOH into the solution. After these steps, potassium salt of Material II is isolated by removing the alcohol and is dispersed in 50 cc of chloroform. 0.01 mole of 4-nitro benzoil chloride is added into the solution and heated and stirred for an hour. Next the following three method steps are performed. First, benzene (100 cc) is added into the reaction solution. The benzene is washed with a mixture of 200 cc of water and 1 mole of sodium hydroxide solution (200 cc). The resultant mixture is distilled, driving off the benzene and the chloroform which is a solvent in the previous step. Finally, recrystallization from the alcohol takes place whereby said Compound 3 in the above table is extracted at the yield rate of 85 weight percent.

The following Table 2 shows the liquid Crystal Operating Temperature Range of the thirty three liquid crystal compounds obtained by the process disclosed in Examples 1 and 2. Those compounds have the general formula,

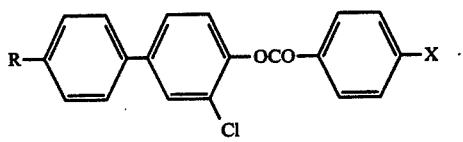

wherein R and X represent as follows:

TABLE 2

| X | R C$_5$H$_{11}$ | C$_6$H$_{13}$ | C$_7$H$_{15}$ | C$_8$H$_{17}$ |
|---|---|---|---|---|
| C$_5$H$_{11}$ | 35°–104° C. | 33°–93° C. | 34°–94° C. | 34°–91° C. |
| C$_6$H$_{13}$ | 43–91 | 25–88 | 25–88 | 39–86 |
| C$_7$H$_{15}$ | 56–98 | 42–86 | 31–88 | 22–88 |
| C$_8$H$_{17}$ | 50–93 | 21–90 | 31–90 | 36–86 |
| C$_9$H$_{19}$ | 41–86 | 41–80 | 38–93 | 27–90 |
| C$_{10}$H$_{21}$ | — | — | — | 47–83 |
| C$_5$H$_{11}$O | 50–126 | 45–118 | — | — |
| C$_6$H$_{13}$O | 57–127 | 35–105 | 62–119 | 57–118 |
| C$_7$H$_{15}$O | — | 37–92 | — | 55–114 |
| C$_8$H$_{17}$O | — | 54–111 | — | 55–115 |
| CN | — | — | — | 101–136 |
| NO$_2$ | — | — | — | 74–104 |

As shown in the Table 2, the liquid crystal compounds of this invention have a broad liquid crystal operating temperature range. If mixed together, however, the results are even better.

For example, equal mixtures by mole of said Compound 1 and said Compound 2 form a liquid crystal composition which has a liquid crystal temperature range of 5°–100° C. and is extremely chemically stable.

As described hereinabove, the compound of the present invention are liquid crystal materials which have a broad liquid crystal temperature range by themselves or when mixed with each other components. The chemical stability has been found to be even better than the biphenyl liquid crystals and ester liquid crystals, thus lending the compounds of the present invention to their use as liquid crystals for display elements, such as watches and the like, and to the use of such LCD in mixtures with biphenyls and ester liquid crystals.

I claim:

1. A liquid crystal compound having the formula:

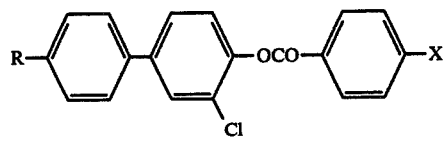

where R represents an alkyl group having five to eight carbon atoms and X represents an alkyl group having five to ten carbon atoms, an alkoxyl group having five to eight carbon atoms, CN or NO$_2$.

2. A compound according to claim 1 wherein R is an alkyl having the formula $C_nH_{2n+1}$ where n equals an integer from 5 to 8.

3. A compound according to claim 1 wherein X is an alkyl having the formula $C_nH_{2n+1}$ where n equals an integer from 5 to 10.

4. A compound according to claim 1 wherein X is an alkoxyl having the formula $C_nH_{2n+1}O$ where n equals an integer from 5 to 8.

5. A compound according to claim 1 wherein X is CN.

6. A compound according to claim 1 wherein X is NO$_2$.

7. A liquid crystal composition comprising mixtures of compounds having the formula:

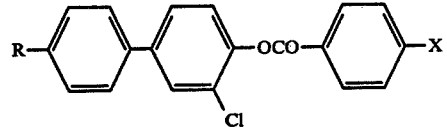

where R represents an alkyl group having five to eight carbon atoms and X represents an alkyl group having five to ten carbon atoms, an alkoxyl group having five to eight carbon atoms, CN or NO$_2$.

* * * * *